United States Patent
Kühnle et al.

(10) Patent No.: US 10,583,253 B2
(45) Date of Patent: Mar. 10, 2020

(54) INJECTION DEVICE

(71) Applicant: VETTER PHARMA-FERTIGUNG GmbH & Co., KG, Ravensburg (DE)

(72) Inventors: Sarah Kühnle, Friedrichshafen (DE); Tobias Kistler, Bergheim (DE); Werner Wurmbauer, Maria Saal (AT); Gerhard Lauchard, Kappel am Krappfeld (AT)

(73) Assignee: VETTER PHARMA-FERTIGUNG GMBH & CO. KG., Ravensburg (DE)

( * ) Notice: Subject to any disclaimer, the term of this patent is extended or adjusted under 35 U.S.C. 154(b) by 75 days.

(21) Appl. No.: 15/534,535

(22) PCT Filed: Nov. 2, 2015

(86) PCT No.: PCT/EP2015/075456
§ 371 (c)(1),
(2) Date: Jun. 9, 2017

(87) PCT Pub. No.: WO2016/091474
PCT Pub. Date: Jun. 16, 2016

(65) Prior Publication Data
US 2017/0319785 A1    Nov. 9, 2017

Related U.S. Application Data

(63) Continuation-in-part of application No. PCT/EP2015/075456, filed on Nov. 2, 2015.

(30) Foreign Application Priority Data

Nov. 2, 2015    (DE) .................. 10 2014 225 687

(51) Int. Cl.
*A61M 31/00*    (2006.01)
*A61M 5/24*    (2006.01)
(Continued)

(52) U.S. Cl.
CPC ...... *A61M 5/2425* (2013.01); *A61M 5/14566* (2013.01); *A61M 5/20* (2013.01);
(Continued)

(58) Field of Classification Search
CPC .... A61M 2005/3158; A61M 2205/323; A61M 5/2425; A61M 5/16831; A61M 5/3146;
(Continued)

(56) References Cited

U.S. PATENT DOCUMENTS

| | | |
|---|---|---|
| 5,879,360 A | 3/1999 | Crankshaw |
| 7,695,456 B2 | 4/2010 | Langley et al. |

(Continued)

FOREIGN PATENT DOCUMENTS

| | | |
|---|---|---|
| DE | 102012204394 A1 | 9/2013 |
| JP | 2007/0512109 A | 5/2007 |

(Continued)

OTHER PUBLICATIONS

English Translation of International Preliminary Report on Patentability and Written Opinion of the International Searching Authority regarding International Application No. PCT/EP2015/075456, dated Jun. 13, 2017. 6 pages.

(Continued)

*Primary Examiner* — Rebecca E Eisenberg
(74) *Attorney, Agent, or Firm* — Stephen T. Olson; Harness, Dickey & Pierce, P.L.C.

(57) ABSTRACT

An injection device has a plunger for displacing a stopper in a syringe or carpule, a holder for the plunger, a drive for the axial displacement of the holder of the plunger, and a control device functionally assigned to the drive. The plunger, or at least a subcomponent thereof, relative to the holder, the holder is able to move over a limited distance relative to the plunger or a subcomponent thereof, opposing a pretensioning force, in that a sensor device is included which detects (Continued)

the relative position of the plunger, or at least a subcomponent thereof, relative to the holder, which comprises at least one sensor element which works together with the control device. The control device is designed such that, upon activation of the sensor element, the speed of advancement of the holder of the plunger is at least reduced.

10 Claims, 2 Drawing Sheets

(51) Int. Cl.
  *A61M 5/20*   (2006.01)
  *A61M 5/145*   (2006.01)
  *A61M 5/31*   (2006.01)
  *A61M 5/315*   (2006.01)
  *A61M 5/14*   (2006.01)

(52) U.S. Cl.
  CPC ........ *A61M 5/2066* (2013.01); *A61M 5/2448* (2013.01); *A61M 5/3146* (2013.01); *A61M 5/31565* (2013.01); *A61M 5/1407* (2013.01); *A61M 5/24* (2013.01); *A61M 2005/2086* (2013.01); *A61M 2005/2418* (2013.01); *A61M 2005/2481* (2013.01); *A61M 2005/31588* (2013.01); *A61M 2205/332* (2013.01)

(58) Field of Classification Search
  CPC ............ A61M 5/61565; A61M 5/2418; A61M 5/2481; A61M 2205/50
  See application file for complete search history.

(56) References Cited

U.S. PATENT DOCUMENTS

| | | |
|---|---|---|
| 7,959,609 B2 | 6/2011 | Gaydos et al. |
| 9,358,336 B2 | 6/2016 | Munk et al. |
| 2003/0158524 A1 | 8/2003 | Langley et al. |
| 2008/0308580 A1 | 12/2008 | Gaydos et al. |
| 2014/0350517 A1 | 11/2014 | Dominguez et al. |
| 2015/0051546 A1 | 2/2015 | Weiss et al. |
| 2015/0080790 A1 | 3/2015 | Munk et al. |

FOREIGN PATENT DOCUMENTS

| | | |
|---|---|---|
| WO | WO-95/20145 A1 | 7/1995 |
| WO | WO-03/061737 A2 | 7/2003 |
| WO | WO-2007/094833 A1 | 8/2007 |
| WO | WO-2013/144152 A1 | 10/2013 |

OTHER PUBLICATIONS

International Search Report (English and German) for PCT/EP2015/075456, ISA/EP, Rijswijk, NL, dated Jan. 28, 2016.
Written Opinion of the ISA (German) for PCT/EP2015/075456, ISA/EP, Rijswijk, NL, dated Jan. 28, 2016.
Search report for parallel Japanese procedure JP2017536928A.

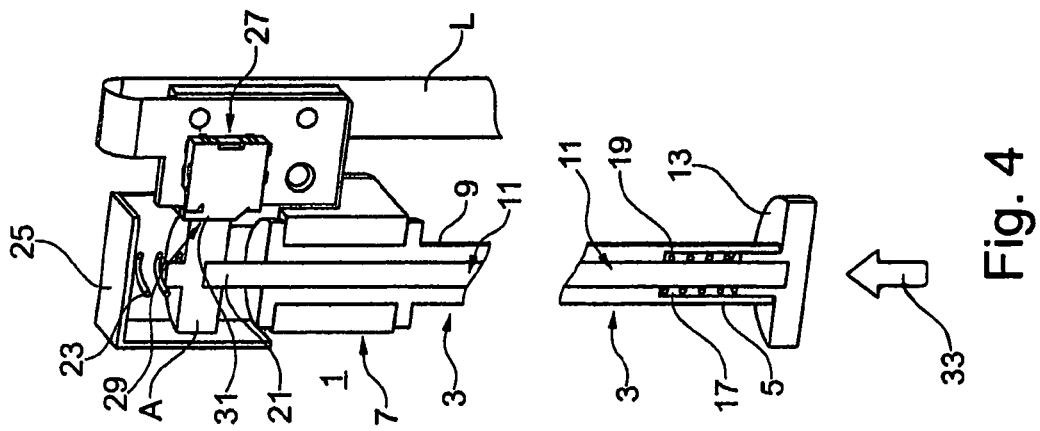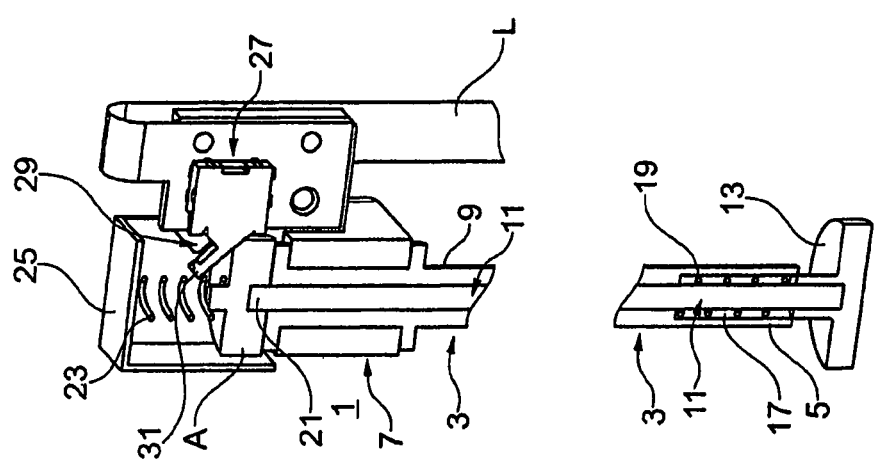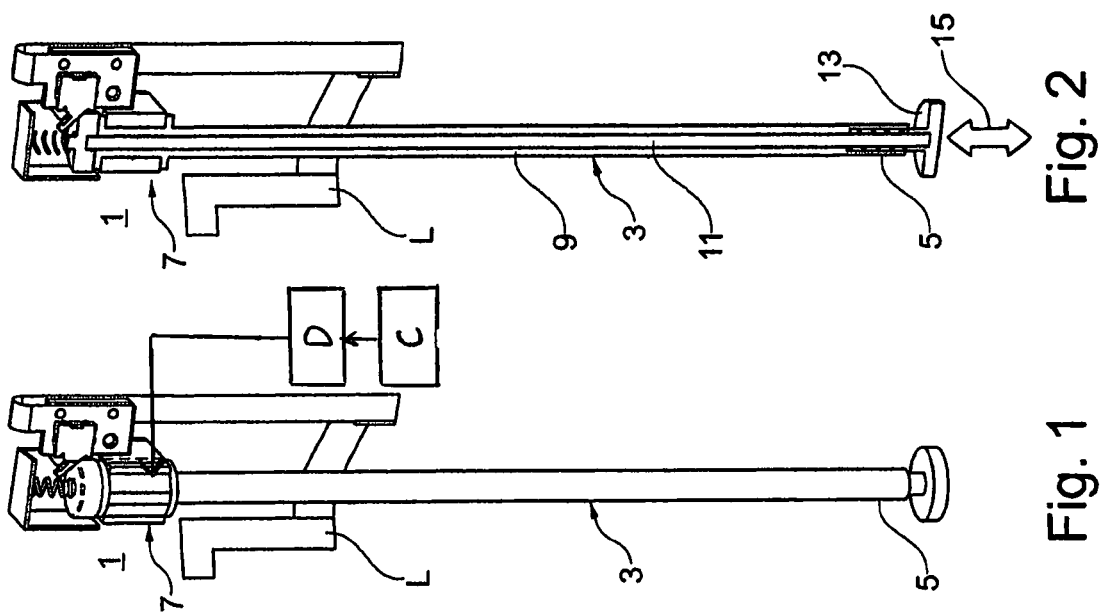

INJECTION DEVICE

CROSS-REFERENCE TO RELATED APPLICATIONS

This application is a 371 U.S. National Stage of International Application No. PCT/EP2015/075456, filed Nov. 2, 2015, which claims the benefit of and priority to German Patent Application No. 102014225687.9, filed on Dec. 12, 2014. The disclosures of the above applications are incorporated herein by reference.

FIELD

The invention relates to a medication device with a cartridge or syringe.

BACKGROUND

Injection devices of the type mentioned here are known. They have a plunger for displacing a stopper in a syringe or carpule, as well as a holder for the plunger and a drive for the axial displacement of the holder of the plunger. The term "axial" is used here to mean that the plunger is moved along its longitudinal extension, and also enters into a syringe or carpule in order to displace at least one stopper in the same. The device also has a control device which works together with the drive and serves to influence the advancement speed of the plunger, and thus of the stopper, inside a syringe or carpule. Preferably, after insertion of a syringe or carpule into the injection device, the plunger is moved with a first speed until a desired position is reached, and after reaching this position, namely after the stopper has been reached, is stopped or moved at a second speed which is lower than the first speed. It has been found that in many cases the injection device moves the stopper before the speed of advancement can be lowered or reduced to zero. As a result, a substance present in the interior of the syringe or carpule can be unintentionally discharged. This can lead to harm for the user, or to a loss of valuable substances.

SUMMARY

The problem addressed by the invention is therefore that of creating an injection device of the above-mentioned type which avoids this disadvantage.

This problem is addressed by an injection device. It is characterized by the fact that it comprises a sensor device which detects the position of the plunger, or at least a subcomponent thereof, relative to the holder. The sensor device has at least one sensor element which works together with the sensor device. The holder is designed to be movable relative to the plunger or at least one subcomponent thereof. In this case, the relative movement occurs against a pretensioning force, specifically over a limited distance. As the holder moves toward the stopper in the syringe or carpule, the plunger or a subcomponent can be halted by a stopper in a syringe or carpule while the holder continues to move forward. The contact of the plunger or of a subcomponent with the stopper can be detected by means of the sensor element before sustained forces of the plunger or of the subcomponent are exerted on the at least one stopper inside the syringe or carpule. This ensures that the same, even if it is positioned inside the syringe or carpule with only small holding forces, is not unintentionally displaced by the injection device. The injection device is further characterized in that the control device is designed such that, upon activation of the sensor element, the drive of the injection device is influenced in such a way that the speed of advancement of the plunger is at least reduced. This ensures that a stopper arranged inside a syringe or carpule is not unintentionally displaced from its initial position at a high speed of advancement after a relative movement of the plunger or a subcomponent relative to the holder has been completed.

The design of the injection device chosen here therefore ensures that, when it is used, the holder is first displaced together with the plunger or a subcomponent thereof in the direction of the at least one stopper of a syringe or carpule. When the at least one stopper is contacted, the plunger or the subcomponent remains stationary, while the holder continues to move forward. This results in a relative movement between the holder and the plunger or its subcomponent, which is detected by the sensor element. During this relative movement, the speed of advancement of the holder can at least be reduced to a desired rate, or even to zero.

In a preferred embodiment of the injection device, the sensor element comprises a microswitch. These require very little installation space, such that the injection device can be made compact. Moreover, such switches are very reliable.

In a particularly preferred embodiment of the injection device, the plunger comprises a base body, and the subcomponent can be displaced relative to the same. The subcomponent can be designed to be very light, such that due to its low mass inertia a displacement can be very fast, the response time of the injection device is very short, and the forces acting on the stopper during the relative movement are very low.

Further designs and advantages of the injection device result from the remaining dependent claims.

BEST DESCRIPTION OF THE DRAWINGS

The invention is explained in more detail below with reference to the drawings, wherein:

FIG. 1 shows a perspective view of a part of a first embodiment of an injection device, the injection device shown operatively associated with a drive and a control device;

FIG. 2 shows a longitudinal section of parts of the injection device shown in FIG. 1;

FIG. 3 shows an enlarged view of a holder having a switch of the injection device according to FIGS. 1 and 2, in a first switch position;

FIG. 4 shows an enlarged view of the switch shown in FIG. 3, in a second switch position;

DETAILED DESCRIPTION

Figure 7:
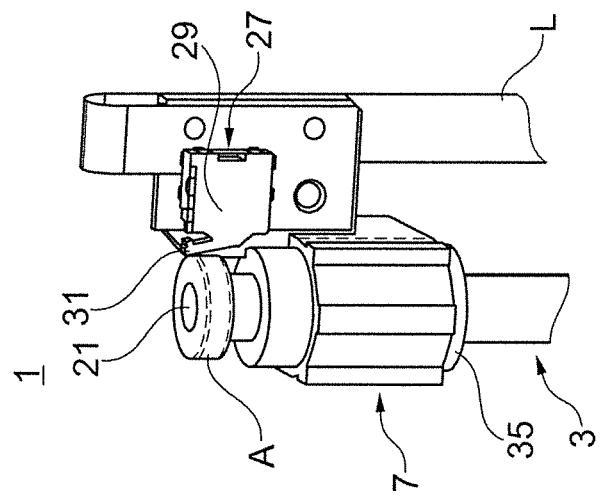
FIG. 7 shows an enlarged view of the switch according to FIG. 6, in a second switch position.

FIG. 1 illustrates parts of a first embodiment of an injection device 1, which is not shown as a whole, specifically a plunger 3 which serves, by means of its lower end in FIG. 1, to displace a stopper which is present in a syringe or carpule which is not shown here, whether to discharge a drug and administer it to a patient, or to mix substances present in a dual-chamber carpule to produce an administration-ready drug. The plunger 3 is mounted on a holder 7 which can be displaced inside the injection device 1 in the direction of the longitudinal extension of the plunger 3, along a guide rail or the like, not shown here. As an example, it is assumed in FIG. 1 that the holder 7 is in an upper starting position, and is displaced downwards in order to displace a stopper.

FIG. 2 shows a longitudinal section of the elements of an injection device 1 shown in FIG. 1. Identical parts are provided with the same reference numerals, such that the description of FIG. 1 is hereby referenced. In the sectional view, it can be seen that the plunger 3 of this embodiment has a base body 9 and a subcomponent 11 which can be displaced relative to the same. The base body 9 in this case is designed as a hollow cylinder having an internal space in which the subcomponent 11, designed in this case as a switch plunger, is displaceably arranged. The base body 9 is fixed in position—that is to say, with respect to the longitudinal extension of the plunger 3, it is non-displaceably connected to the holder 7. Thus, when the holder 7 is moved up and down, the plunger 3, and therefore its base body 9, moves up and down synchronously with the holder 7.

FIG. 2 also shows that the switch plunger—that is, the subcomponent 11—projects beyond the lower end 5 of the base body 9 and has a plate 13 at its lower end, which rests on a stopper which will be displaced when the holder 7, together with the plunger 3, is moved downwards per the double arrow 15 into the interior of a syringe or carpule.

An upward movement of the holder 7 is then particularly initiated when the drug present in the syringe or carpule has been completely administered, and a new syringe or carpule is to be inserted into the injection device. As a rule, the stopper is released after each injection by the holder 7 being moved slightly backward, i.e. upwards, by the plunger rod 3.

FIG. 3 shows, on an enlarged scale, both the region of the holder 7 of the injection device 1 and also the lower end 5 of the plunger 3, with the disk 13 attached to the subcomponent 11 which is designed as a switch plunger. Identical parts are provided with the same reference numerals, such that the above figures and descriptions are hereby referenced.

It can be seen from the enlarged depiction of the lower end 5 of the plunger 3 that its base body 9 has, on the one hand, an internal space for accommodating the second subcomponent 11—that is to say, the switch plunger—and on the other hand an enlarged region 17 which serves to receive a pretensioning element embodied as a helical spring 19. This is supported on an upper edge of the region 17 and, on the other hand, on the disk 13, under pretension, such that the same is held at a maximum distance from the lower end 5 of the plunger 3, wherein a force which is directed downward in FIG. 3 is therefore applied to the subcomponent 11. In a suitable manner, the second subcomponent 11 is prevented from being pushed out of the base body 9 by the pretensioning element 19. In the embodiment illustrated here, there is a limit stop A on an upper end 21 of the subcomponent 11, which is annular in shape in this example, and is large enough so that it cannot be displaced downward through the internal space of the base body 9. The limit stop A rests on the upper side of the holder 7, so that the pretensioning element 19 can press out the second subcomponent 11, with the disk 13, only over a predetermined distance.

A spring element 23 acts on the upper end 21 of the subcomponent 11, which in this case is again designed as a helical spring, and is supported on one end thereof, under tension, on the upper end 21, and on the other end on a counter bearing 25 of the holder 7. As a result of the pretensioning of the spring element 23, the second subcomponent 11—as is already the case, due to the pretensioning element 19—is pushed downward relative to the base body 9 of the plunger rod 3, which is fixed to the holder 7.

The pretensioning element 19 can be dispensed with given an appropriate design. Accordingly, it is possible that there is only the pretensioning element 19, and not the spring element 23.

The injection device 1 also has a sensor device 27 which comprises a sensor element 29, which in this case has a microswitch and a switch arm 31 located in the path of movement of the upper end 21 of the second subcomponent 11. The latter is arranged in such a way that it is pivoted out of its starting position and/or first switch position, shown in FIG. 3, upon an upwardly directed displacement of the second subcomponent 11—that is, the switch plunger—into a second position or second shift position.

It is possible to configure the sensor device, with the sensor element 29 and/or the microswitch, on the upper end 21 of the second subcomponent 11, and to ensure that the actuating arm 31 works together with a counter bearing which is fixed to the holder 7. The construction provided here, however, is characterized in that the sensor element 29 is fixed in position on the holder 7, and in that its actuating arm 31 is actuated by the subcomponent 11, which is able to move relative to the base body 9 of the plunger 3. The plunger 3 is therefore lighter.

The explanations make clear that, instead of the microswitch, or in addition thereto, other devices such as magnetic tapes, light barriers or the like can be used to detect a particular position of the subcomponent 11 with respect to the holder 7.

FIG. 4 again shows an enlarged detail of the injection device 1, specifically the upper end 21 of the plunger 3 with the holder 7, and the lower end 5 of the plunger 3 with the disk 13. Identical parts are provided with the same reference numerals, such that the above figures and descriptions are hereby referenced.

The holder 7 is displaced downwards together with the plunger 3 into a syringe or carpule until the disk 13 strikes a stopper in a syringe or carpule, such that, as indicated by the arrow 33, the disk 13 is moved upwards relative to the base body 9 of the plunger 3, opposing the pretension of the pretensioning element 19. During this movement, the spring element 23 also acts on the disk 13. Immediately after the disk 13 touches a stopper of a syringe or carpule, the described relative movement of the subcomponent 11 connected to the disk 13 takes place, relative to the base body 9 of the plunger 3, while the holder 7 continues to move further towards the stopper. The upward movement of the disk 13 and of the first subcomponent 11, with the aid of a force indicated by the arrow 33, is terminated by the disk 13 abutting against a limit stop—in this case at the lower end 5 of the plunger 3, as shown in FIG. 4.

It is also apparent from FIGS. 1 to 4 that the electrical supply to the sensor device 27 and to the sensor element 29 takes place via a conductor path L, which is of a flexible design so that it can follow the holder 7 while the same is moved, together with the plunger 3, inside the injection device 1 in the direction of the longitudinal extension of the plunger 3.

The conductor path L is connected on one end thereof to a power supply; on the other hand it serves to relay signals from the sensor element 29—in this case, therefore, switching signals of the microswitch—to a control device C by means of which a drive D which effects the upward and downward movement of the holder 7 is influenced.

Figure 5:
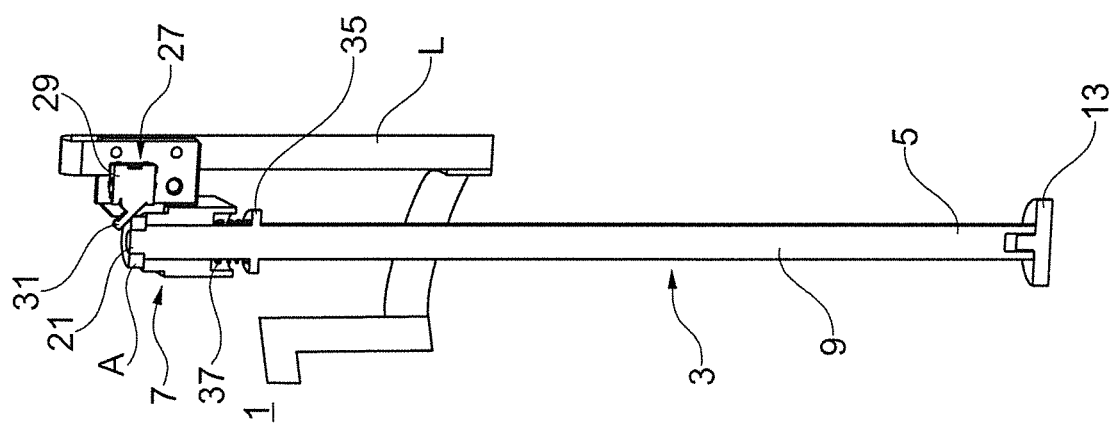
FIG. 5 shows a modified embodiment of parts of an injection device in a longitudinal section.

FIG. 5 shows a modified embodiment of the elements of an injection device 1 shown in FIG. 1. Identical and functionally equivalent parts are provided with the same reference numerals.

FIG. 5 corresponds to the illustration in FIG. 2: the plunger 3 of the injection device 1, as well as the holder 7, are shown in longitudinal section. The plunger 3 is designed in this case as a solid element—that is, is not hollow. On its lower end 5, it carries a disk 13—which is not absolutely necessary in this case as in the embodiment illustrated above—but which serves to ensure that the lower end 5 properly detects the stopper present in a syringe or carpule, for example if it is to be equipped with a central bore.

In contrast to the first embodiment, the plunger 3 itself is displaceably mounted inside the holder 7. Therefore, in the direction of its longitudinal extension, it can execute a relative movement inside the holder 7 and relative to the same. The plunger 3 is configured, in the region of its upper end 21 and below the holder 7, with a counter bearing—in this case, a circumferential collar 35—on which a spring element 37 is supported, the same being designed in this case as a helical spring which runs around the base body 9 of the plunger 3, extends into the internal space of the holder 7, and is supported thereon. The spring element 37 is pretensioned so that it exerts a downward force on the plunger 3. The plunger 3 is prevented in a suitable manner from slipping out of the holder 7 downwards. Here, by way of example, a preferably annular limit stop A is included, which is attached at the upper end 21 above the holder 7 such that the upper end 21 cannot yield downwards through the internal space of the holder 7 even if the spring element 37 is exerting a pretension on the plunger 3.

The circumferential collar 35 on the plunger 3 is designed in such a way that, although a relative movement between the holder 7 and the plunger 3 is possible, the travel distance of this movement is limited. The holder 7 can only move downwards relative to the plunger 3 until it abuts against a limit stop—in this case, the collar 35.

In the embodiment of the injection device 1 shown in FIG. 5 as well, a sensor device 27 is included, which comprises a sensor element 29, which in this case again comprises a microswitch with an actuating arm 31. The actuating arm 31 is arranged in the movement path of the plunger 3, as in the embodiment described above, in such a way that, when the plunger 3 moves relative to the holder 7, the actuating arm 31 is deflected upward by the upper end 21 of the plunger 3, and the sensor element 29 is thereby activated.

Figure 6:
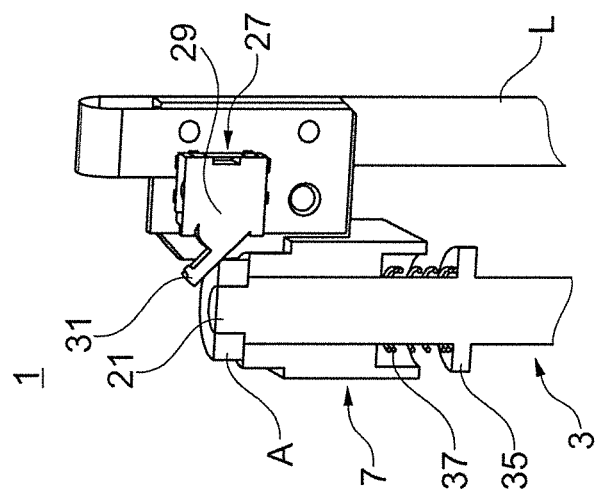
FIG. 6 shows an enlarged view of a holder having a switch of the injection device according to FIG. 5, in a first switch position.

FIG. 6 shows the holder 7 and the upper end 21 of the plunger 3 of the injection device 1 in an enlarged view, in the first functional position. Identical parts are provided with the same reference numerals so that reference is accordingly made to the preceding description.

FIG. 6 again clearly shows that the spring element 37 is supported on one end thereof in the internal space of the holder 7 and, on the other end, in the counter bearing of the plunger 3, which in this case is designed as a circumferential collar 35. Due to its pretensioning, the spring element 37 presses the plunger 3 into its lowest position, which is defined by the limit stop A at the upper end 21 of the plunger 3. This then receives the plunger 3 when there is no force acting on it from below. The actuating arm 31 is not actuated in this functional position.

FIG. 7 shows the elements of the injection device 1 shown in FIG. 6, in a second functional position. Identical parts are provided with the same reference numerals so that reference is accordingly made to the preceding description. Contrary to FIG. 6, however, the holder 7 is not shown in the longitudinal section but in a side view, as is the plunger 3.

It can be seen that when the holder 7 is moved downward, and the plunger 3 follows, the same can halt against a stopper in a syringe or carpule, such that a force acting from below is applied to the plunger 3, which is indicated by the arrow 33.

As a result of this force, the plunger 3 is displaced upwards relative to the holder 7, specifically against the pretensioning force of the spring element 37, which is compressed during the movement of the plunger 3 relative to the holder 7. In this case, the upper end 21 of the plunger 3 is also moved upwards together with the limit stop A, such that the actuating arm 31 of the sensor element 29, which is designed here as a microswitch, is pivoted upwards toward the sensor device 27. It therefore moves from the first switch position shown in FIG. 6 into the second switch position shown in FIG. 7. The sensor element 29 is therefore actuated, such that a corresponding signal is emitted via the conductor path L to the control device, not shown here, of the drive. It will be appreciated that instead of the microswitch or in addition to the same, other devices can also be used, as has also been noted in connection with the explanations of FIG. 3.

As mentioned above, the upward movement of the plunger 3 relative to the holder 7 is limited, specifically by the collar 35 abutting against the holder 7 from below.

The following describes the function of the injection device 1 and the elements illustrated in FIGS. 1 to 7 in more detail:

Injection devices 1 of the type described here serve to move a stopper present in a syringe or carpule by means of a plunger 3, specifically and typically in such a manner that the internal volume of the syringe and/or carpule is reduced and substances present therein are discharged. For this purpose, a syringe or a carpule is inserted into the injection device 1 and oriented in such a manner that it is positioned coaxially with the plunger 3, such that the plunger 3 can enter the internal space of the syringe or carpule and can displace the stopper.

Injection devices 1 of the type mentioned here are also used in connection with known dual-chamber carpules, wherein the internal space thereof is usually sealed by an end stopper, and a second so-called center stopper divides the internal space into two subspaces in which various medicinal substances can be present, including water suitable for injections. In the case of dual-chamber carpules, the end stopper is first moved a certain distance, wherein an overpressure arises in the subspace between this stopper and the central stopper, such that the center stopper is moved in the same direction as the end stopper. Finally, the center stopper reaches the area of a bypass on the inner surface of the carpule, such that the two substances present in the separate subspaces can mix.

Typically, the plunger 3 of the injection device 1 is in its maximum retracted position. As a result, the syringe or carpule can be easily inserted into the injection device 1. Then the plunger 3 is then displaced together with the holder 7 in such a way that the lower end 5 of the plunger 3—optionally a disk 13 present in this case—is moved towards the at least one stopper in the syringe or carpule. The speed of advancement is comparatively high in this case, in order to save time in this operating phase of the injection device 1. The plunger 3 is usually immediately stopped, or continues to move forward at a reduced speed, as soon as it touches the stopper in the syringe or carpule for the first time. For this purpose, it is necessary to detect the moment when the plunger 3 touches the stopper. Due to the technical characteristics of known injection devices, it is often the case that, even if the drive 7 of the holder 7 is immediately inactivated, the latter continues to move together with the plunger 3 in the original movement direction, and a force is exerted on the stopper. This is therefore moved in an uncontrolled manner. As a result, a substance present in a syringe or carpule can be discharged.

In the embodiments shown here, the holder 7 can perform a movement relative to the plunger 3 or its subcomponent 11 as soon as the plunger 3 or the subcomponent 11 is stopped by the stopper. The plunger 3 and/or the subcomponent 11 is subjected to a pretensioning force which keeps it in a defined position relative to the holder 7. The pretensioning force is designed in such a way that the forces acting on the stopper are not sufficient to displace the latter.

If the holder 7 and the plunger 3 are moved, out of an initial position at a distance from a syringe or carpule, in the direction of their stoppers, both the holder 7 and the plunger 3, which can also comprise a subcomponent 11, are first synchronously moved into the syringe or the carpule. As soon as the plunger 3 or a subcomponent 11 thereof comes into contact with the stopper of the syringe or carpule and is not further displaced, the holder 7 is displaced, opposing a pretensioning force, relative to the stationary plunger 3, as explained in FIGS. 5 to 7. A corresponding movement occurs in the embodiment according to FIGS. 1 to 4: In this case, the holder 7 moves relative to a subcomponent 11 of the plunger 3, which here is designed as a switch plunger, when in contact with the stopper.

Therefore, in both embodiments, a subcomponent 11 of the plunger 3 and/or the plunger 3 itself remains stationary as soon as the stopper is contacted. A further forward movement of the subcomponent 11 and/or of the plunger 3 does not take place even if the holder 7 moves further in the direction towards the stopper, because the pretensioning force exerted on the plunger 3 or the subcomponent 11 is so small that the stopper cannot be moved by this alone.

As soon as the plunger 3 or its subcomponent 11 touches and stops the stopper in the syringe or carpule during an advancing movement of the holder 7, the sensor element 29—in this case, an actuating arm 31 of a microswitch—is displaced from a first switch position into a second switch position, such that a switching signal is transmitted to the control device which works together with the drive. By means of this signal, the drive is deactivated—that is, a motor, in particular an electric motor, is stopped immediately by the current being switched off, optionally by short-circuiting. It is also possible to terminate the advancing movement of the holder 7 as quickly as possible to effect a reversal of the direction of rotation of the motor. In spite of the mass inertia of the holder 7 and the reaction inertia of the drive, the holder 7 does not exert any force on the stopper inside the syringe or carpule because the holder 7 initially moves relative to a subcomponent 11 or the plunger 3, and no force is exerted on the stopper by the same. During the relative movement of the holder 7 with respect to the subcomponent 11 and/or the plunger 3, only the pretensioning force of a spring element or of a pretensioning element acts on the part contacting the stopper—i.e., the plunger 3 and/or its subcomponent 11. This pretensioning force is so small, due to the sizing of the spring element and/or pretensioning element, that even stoppers which can be displaced very easily inside a syringe or carpule, and which are held in their initial position only by frictional forces, are not displaced inside the syringe or carpule by this pretensioning force.

The movement of the holder 7 relative to the plunger 3 and/or its subcomponent 11 causes the upper end 21 of the plunger 32 and/or the subcomponent 11 to interact with the sensor element 29. In this case, the upper end 21, preferably the limit stop A configured there, interacts with an actuating arm 31 of the sensor element 29 constructed as a microswitch. The actuating arm 31 is moved out of its first switch position as shown in FIGS. 3 and 6, actuated upon the impact of the stopper 3 or the subcomponent 11, and moved into its second switch position as shown in FIGS. 4 and 7. As a result, a signal is emitted to the control unit, and via the latter to the drive of the injection device. As soon as this has occurred, the drive is disabled and the advancement of the holder 7 is at least reduced, or is stopped.

It was mentioned above that a relative movement between the holder 7 and the plunger 3 and/or the subcomponent of the same is possible for a limited distance—specifically up until the plunger 3 and/or the subcomponent 11 thereof has reached the associated limit stop. The time required to reach the limit stop is sufficient to at least reduce the speed of advancement of the holder 7, as desired. Only when the limit stop is reached does the holder 7 exert a force on the stopper in the syringe or carpule which is greater than the pretensioning force acting on the plunger 3 and/or the subcomponent 11 thereof.

At this point it is possible that a user initiates a further movement of the holder 7 in the direction of the previous movement, in order to mix the substance present in the subspaces of the dual-chambered carpule in the event that a dual-chambered carpule is being used, to therefore prime a drug present in the carpule. Subsequently, the user can initiate the injection of the prepared drug by again activating the drive and the advancement of the holder.

In another embodiment of the injection device, the control device of the drive is designed in such a manner that, after a switching signal has been received from the sensor element, the holder 7 and/or the plunger 3 and its subcomponent 11 is/are automatically further advanced, preferably at a reduced speed, in order to automatically prime the drug present in a dual-chambered carpule. When this is done, the holder 7 is then only activated again once the user wishes to do so, and accordingly activates the injection device 1.

In general, the holder 7 with the plunger 3 and the optionally-included subcomponent 11 therefore advances relatively rapidly. As soon as a stopper is detected, which is done by the sensor element 29, the advancement of the holder 7 is first stopped. During the priming of a drug in a dual-chamber carpule, which is currently taking place, a defined slow advancement of the holder together with the plunger and, optionally, its subcomponent takes place until a center stopper in the dual-chamber carpule passes into the region of a bypass. The priming process is carried out by a further advancement, wherein substances present in the subspaces of the dual-chamber carpule are mixed and/or activated during this priming process. During the mixing and/or activating of the substances, the advancement is preferably stopped. Thereafter, the drive of the holder 7 is again activated to advance the stopper inside the carpule by the plunger 3 or its subcomponent 11 at a desired rate, in order to administer the prepared drug.

The possibility of the relative movement between the holder 7 and the plunger (FIGS. 5 to 7) and/or a subcomponent 11 of the plunger 3 (see FIGS. 1 to 4) has the consequence that the injection device 1 does not exert any substantial forces on the stopper inside a syringe or carpule during a first time period after contact of the stopper. The forces applied by the holder 7 only act on the stopper when the holder 7 has executed a movement relative to the plunger 3 or a subcomponent 11 of the same over a defined distance. The time required for this is utilized to stop and/or to influence the drive of the holder 7 in such a manner that the holder 7 is moved at a slower, defined speed of advancement.

The invention claimed is:

1. An injection device comprising:
   a plunger for displacing a stopper in a medical hollow device, the plunger having a base body and a subcomponent;
   a holder for the plunger, the holder being axially displaceable;
   a control device for functional assignment to a drive; and
   a sensor device for detecting a relative position of the plunger or the subcomponent relative to the holder, the sensor device including at least one sensor element which works together with the control device,
   wherein the holder is able to move over a limited distance relative to the plunger or a subcomponent thereof to oppose a pretensioning force,
   wherein the control device is designed in such a manner that, upon activation of the sensor element, a speed of advancement of the holder of the plunger is at least reduced,
   wherein the subcomponent of the plunger is movable relative to the base body, and
   wherein the base body of the plunger is a hollow cylinder comprising an internal space, and the subcomponent is a switch plunger arranged to allow movement in the internal space.

2. The injection device according to claim 1, wherein the at least one sensor element comprises a microswitch.

3. The injection device according to claim 2, wherein the microswitch is actuated by the plunger or by the subcomponent of the plunger.

4. The injection device according to claim 3, wherein the microswitch is actuated when a defined relative position of the plunger or of the subcomponent of the plunger relative to the holder is reached.

5. The injection device according to claim 1, wherein the holder has a spring element which biases the plunger or the subcomponent into a first functional position.

6. The injection device according to claim 5, wherein the plunger is mounted on the holder in such a manner that the plunger or the subcomponent, upon contact of a stopper in a syringe or carpule, is moved against the force of the spring element out of the first functional position.

7. The injection device according to claim 1, wherein the control device is designed such that the drive of the injection device, and therefore the holder of the plunger, are stopped when the sensor element is activated.

8. The injection device according to claim 1, wherein the control device is designed such that, when the sensor element is activated, advancement of the holder of the plunger is stopped, and then the advancement of the holder is continued at a reduced speed.

9. An injection device comprising:
   a plunger for displacing a stopper in a medical hollow device the medical hollow device selected from a group consisting of a syringe and a carpule, the plunger having a base body and a subcomponent;
   a holder for the plunger, the holder being axially displaceable;
   wherein the holder is able to move over a limited distance relative to the plunger or the subcomponent to oppose a pretensioning force,
   wherein the subcomponent of the plunger is movable relative to the base body, and
   wherein the base body of the plunger is a hollow cylinder comprising an internal space, and the subcomponent is a switch plunger arranged to allow movement in the internal space.

10. The injection device according to claim 9, further comprising a sensor element and a control device for functional assignment to a drive, wherein the control device is designed in such a manner that, upon activation of the sensor element, a speed of advancement of the holder of the plunger is at least reduced.

* * * * *

UNITED STATES PATENT AND TRADEMARK OFFICE
CERTIFICATE OF CORRECTION

PATENT NO. : 10,583,253 B2
APPLICATION NO. : 15/534535
DATED : March 10, 2020
INVENTOR(S) : Sarah Kühnle et al.

It is certified that error appears in the above-identified patent and that said Letters Patent is hereby corrected as shown below:

On the Title Page

(30) Foreign Application Priority Data should read:
December 12, 2014 (DE) ........................... 10 2014 225 687

Signed and Sealed this
Ninth Day of July, 2024

Katherine Kelly Vidal
*Director of the United States Patent and Trademark Office*